United States Patent
Fisher

(10) Patent No.: US 6,869,760 B2
(45) Date of Patent: Mar. 22, 2005

(54) USE OF PROSTATE TUMOR INDUCING GENE FOR DETECTION OF CANCER CELLS

(75) Inventor: Paul B. Fisher, Scarsdale, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/263,981

(22) Filed: Mar. 5, 1999

(65) Prior Publication Data

US 2002/0155437 A1 Oct. 24, 2002

Related U.S. Application Data

(63) Continuation of application No. PCT/US97/15645, filed on Sep. 5, 1997, which is a continuation-in-part of application No. 08/708,208, filed on Sep. 6, 1996, now abandoned, which is a continuation-in-part of application No. 08/371,377, filed on Jan. 11, 1995, now Pat. No. 5,851,764.

(51) Int. Cl.$^7$ .......................... C12Q 1/68; C12P 19/34
(52) U.S. Cl. ........................................ 435/6; 435/91.2
(58) Field of Search ............................. 435/5, 6, 91.2

(56) References Cited

U.S. PATENT DOCUMENTS

| | | | |
|---|---|---|---|
| 5,162,504 A | 11/1992 | Horoszewicz | |
| 5,227,471 A | 7/1993 | Wright | |
| 5,314,996 A | 5/1994 | Wright | |
| 5,851,764 A | * 12/1998 | Fisher et al. | 324/6 |
| 6,200,765 B1 | * 3/2001 | Murphy et al. | 435/7.23 |

FOREIGN PATENT DOCUMENTS

WO 9621671 7/1996

OTHER PUBLICATIONS

Su Z et al., 1996, "Surface–epitope masking and expression cloning identifies the human prostate carcinoma tumor antigen gene PCTA–1 a member of the galectin gene family" *Proc. Natl. Acad. Sci. USA* 93: 7252–7257.

Lin J et al., 1996, "The 5'–UTR of prostate tumor inducing gene–1, PTI–1, is transcriptionally activated during oncogenic transformation" Proceedings Am. Assoc. Cancer Res. Ann. 37:146 (abstract 1008).

Veronese ML et al., 1996, "The t(6;16)(p21;q22) chromosome translocation in the LNCaP prostat carcinoma cell line results in tpc/hpr fusion gene" *Cancer Res.* 56:728–732.

Cama C et al., 1995, "Molecular staging of prostate cancer II. A comparison of the application of an enhanced reverse transcriptase polymerase chain reaction assay for prostate specific antigen versus prostate specific membrane antigen" *J. Urol.* 153:1373–1378.

Chastel C, 1995, "Links and interactions between mycoplasmas and viruses: past confusions and present realities" *Arch. Virol.* 140:811–826.

Jiang H et al., 1995, "The melanoma differentiation–associated gene mda–6, which encodes the cyclin–dependent kinase inhibitor p21, is differentially expressed during growth, differentiation and progression in human melanoma cells" *Oncogene* 10:1855–1864.

Shen R et al., 1995, "Identification of the human prostatic carcinoma oncogene PTI–1 by rapid expression cloning and differential RNA display" *Proc. Natl. Acad. Sci. U.S.A.* 92:6778–6782.

Tsai S et al., 1995, "Mycoplasmas and oncogenesis: persistent infection and multistage malignant transformation" *Proc. Natl. Acad. Sci. U.S.A.* 92:10197–10201.

Israeli RS et al., 1994, "Sensitive nested reverse transcription polymerase chain reaction detection of circulating prostatic tumor cells: comparison of prostate–specific membrane antigen and prostate–specific antigen–based assays" *Cancer Res.* 54:6306–6310.

Katz AE et al., 1994, "Molecular staging of prostate cancer with the use of an enhanced reverse transcriptase–PCR assay" *Urol.* 43:765–775.

Nakhla AM et al., 1994, "Characterization of ALVA–4 cells, a new human prostatic cancer cell line" *Steroids* 59(10):586–589.

Crozat A et al., 1993, "Fusion of CHOP to a novel RNA–binding protein in human myxoid liposarcoma" *Nature* 363:640–644.

Epstein JI et al., 1993, "Correlation of pathologic findings with progression after radical retropubi prostatectomy" *Cancer* 71:3582–3593.

Jiang H et al., 1993, "Use of a sensitive and efficient subtraction hybridization protocol for the identification of genes differentially regulated during the induction of differentiation in human melanoma cells" *Mol. Cell. Different.* 1(3):285–299.

(List continued on next page.)

Primary Examiner—Kenneth R. Horlick
(74) Attorney, Agent, or Firm—Baker Botts L.L.P.

(57) ABSTRACT

This invention provides a method for detecting cancer cells in a sample comprising detection of the expression of a Prostate Tumor Inducing Gene in the sample, wherein a positive detection of the expression indicates the presence of cancer cells in the sample. In an embodiment, the expression is performed by measuring the level of PTI mRNA. The mRNA is measured by reverse transcription-polymerase chain reaction using at least a pair of appropriate primers. It is well known in the art that once the sequence of the Prostate Tumor Inducing Gene is determined, appropriate pair of primers may be selected. This invention also provides the above method, wherein the expression is performed by measuring the level of PTI protein. The level of PTI protein is measured by steps of: a) contacting the sample with antibody capable of specifically recognizing PTI-1 protein under conditions permitting formation of complexes between the PTI-1 protein and the antibody; and b) measuring the complex formed, thereby measuring the level of PTI-1 protein expressed in the cancer cells.

13 Claims, 7 Drawing Sheets

OTHER PUBLICATIONS

Lu–Yao GL et al., 1993, "An assessment of radical prostatectomy. Time trends, geographic variation and outcomes. The Prostate Patient Outcomes Research Team" *JAMA 269*:2633–2636.

Liang R et al., 1992, "Differential display of eukaryotic messenger RNA by means of the polymerase chain reaction" *Science* (Washington DC) *257*:967–971.

Su Z et al., 1992, "Transfer of a dominant–acting tumor–inducing oncogene from human prostatic carcinoma cells to cloned rat embryo fibroblast cells by DNA–transfection" *Anticancer Res. 12*:297–304.

Noller HF, 1991, "Ribosomal RNA and translation" *Annu. Rev. Biochem. 60*:191–227.

Mukamel E et al., 1987. "Pitfalls in preoperative staging in prostate cancer" *Urol. 30*:318–323.

Salo JO et al., 1987, "Computerized tomography and transrectal ultrasound in the assessment of local extension of prostatic cancer before radical retropubic prostatectomy" *J. Urol. 137*:435–438.

Shima ZA et al., 1986, "Gene encoding the a chain of the T–cell receptor is moved immediately downstream of c–myc in a chromosomal 8;14 translocation in a cell line from a human T–cell leukemia" *Proc.Natl. Acad. Sci. U.S.A. 83*:3439–3443.

Watt KWK et al., 1986, "Human prostate–specific antigen: structural and functional similarity wit serine proteases" *Proc. Natl. Acad. Sci. U.S.A. 83*:3166–3170.

Wang MC et al., 1979, "Purification of a human prostate specific antigen" *Invest. Urol. 17*:159–163.

* cited by examiner

| | | |
|---|---|---|
| Primer | UU (5'UTR Upper): | 5' ACCCGAGAGGGGAGTGAAATA 3' |
| Primer | UL (5'UTR Lower): | 5' TGCCGCCATTCCACATTCAGT 3' |
| Primer | BU (Bridge Upper) | 5' ATGGGGTAGAGCACTGAATG 3' |
| Primer | BL (Bridge Lower) | 5' AACACCAGCAGCAACAATCAG 3' |
| Oligonucleotide | BSP (Bridge Specific Probe) | 5' AAATTAAGCTATGCAGTCGG 3' |

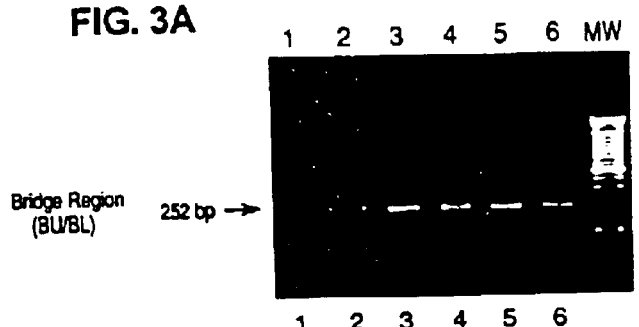
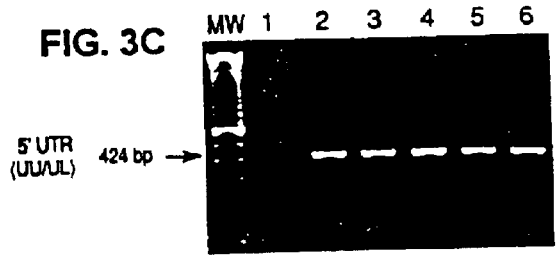
FIG. 3A
FIG. 3B
FIG. 3C
MW = Molecular Weight Markers
1 = CREF-Trans 6
2 = CREF-Trans 6:4 NMT
3 = LNCaP
4 = DU-145
5 = T47D
6 = SW480

RT-PCR of GAPDH 1 2 3 4 5 6 7 8 9 10 11 12 13 14 15 16 17 18

19 20 21 22 23 24 25 26 27 28 29 30 31 32 33

RT-PCR of BRIDGE REGION (BU AND BL)

RT-PCR of 5' UTR 1 2 3 4 5 6 7 8 9 10 11 12 13 14 15 16 17 18

19 20 21 22 23 24 25 26 27 28 29 30 31 32 33

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 1
acccgagagg ggagtgaaat a                                               21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 2
tgccgccatt ccacattcag t                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 3
atgggggtag agcactgaat g                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
aacaccagca gcaacaatca g                                               21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: probe

<400> SEQUENCE: 5
aaattaagct atgcagtcgg                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 6
gagtctgaat agggcgactt                                                 20

<210> SEQ ID NO 7
<211> LENGTH: 20

```
<212> TYPE: DNA
<213> ORGANISM: Artificial Sequence
<220> FEATURE:
<223> OTHER INFORMATION: Description of Artificial Sequence: primer

<400> SEQUENCE: 7
agtcagtaca gctagatgcc                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 8
tacccactgc atcaggaaca                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 9
ccttgaagca caccattaca                                              20
```

USE OF PROSTATE TUMOR INDUCING GENE FOR DETECTION OF CANCER CELLS

This application is a continuation of PCT International Application No. PCT/US97/15645, filed Sep. 5, 1997, designating the United States of America, which is a continuation-in-part of U.S. application Ser. No. 08/708,208 filed Sep. 6, 1996 (abandoned), which is a continuation-in-part of application Ser. No. 08/371,377 filed Jan. 11, 1995 (now U.S. Pat. No. 5,851,764), the contents of which are incorporated in their entireties into the present application.

BACKGROUND OF THE INVENTION

Rapid expression cloning and differential RNA display identifies a gene, prostate tumor inducing gene-1 (PTI-1), that is differentially expressed in prostate cancer versus normal prostate and benign prostatic hypertrophy. PTI-1 encodes a truncated and mutated human elongation factor 1α (EF-1α), and its 5' untranslated (UTR) region shares significant homology with the 23S ribosomal RNA gene of *Mycoplasma hyopneumoniae*. PCR with human genomic DNAs, using PTI-1 5' UTR specific primers, suggests that this sequence is part of the human genome. Furthermore, RT-PCR, with one primer specific to the 5' UTR region and the other to the EF-1a coding region, amplifies PTI-1 transcripts from total RNA of various human tumor cell lines and blood samples from prostate carcinoma patients. RT-PCR products with the predicted size and sequence of PTI-1 are detected in RNAs from cell lines of human prostate, breast and colon carcinomas. This RT-PCR product is shown by Southern blotting and sequence analyses to contain the junction sequence between the 5' UTR and the coding region of the PTI-1 gene. Furthermore, RT-PCR analysis indicates that the PTI-1 gene is also expressed in prostate carcinoma patient derived blood samples. On the basis of serial dilution experiments, PTI-1 can detect 1 prostate carcinoma cell in $10^8$ cells not expressing PTI-1. In this context, PTI-1 represents the most sensitive marker currently available for detecting human prostate cancer. This study confirms the authenticity of the PTI-1 gene and documents its potential clinical utility as a sensitive and specific indicator of prostate cancer progression.

Adenocarcinoma of the prostate is presently the most prevalent internal cancer of men in the United States and the second most frequent cause of cancer-related deaths. Current methodologies for the early detection of prostate cancer, including physical examination, monitoring PSA[3] levels, tissue biopsy, ultrasound and bone scans, are restricted in both sensitivity and specificity (1–3). In addition, present testing modalities do not permit a distinction between cancers that will remain indolent and those which will prove aggressive and life threatening (1–4). Using DNA transfection approaches with a novel acceptor cell line, CREF-Trans 6 (5), and the molecular approach of differential RNA display (6), a novel putative prostatic carcinoma tumor inducing oncogene, PTI-1, has been identified and cloned from a human prostate carcinoma, LNCaP, cDNA library (7). Using RT-PCR approaches with primers corresponding to the 5' UTR region of PTI-1, expression is detected in 15 of 16 carcinomas of the prostate, but not in normal prostate or BPH tissue (7). Although further testing with a larger number of patient samples is clearly needed, these provocative results suggest that PTI-1 monitoring might prove beneficial in prostate cancer diagnostics.

The full-length PTI-1 cDNA is 2,123 bp and it encodes a truncated and mutated human EF-1α (7) (FIG. 1). The structure of the PTI-1 cDNA is unique in that its 5' UTR shares significant homology (approximately 85%) with the prokaryotic 23S ribosomal RNA gene from Mycoplasma hyopneumoniae. This high degree of sequence homology between the 5' UTR of the PTI-1 gene and prokaryotic 23S ribosomal RNA gene raises concerns that contamination by bacteria in the LNCaP cell culture used to prepare the cDNA library and subsequent cloning artifacts may be responsible for the identification of the PTI-1 gene. Confirming the authenticity of the PTI-1 gene is mandatory before further studies can be conducted to elucidate any potential role of PTI-1 in human prostate cancer development and evolution.

In the present study, the question of the validity of the PTI-1 gene was addressed by analyzing its presence in the human genome, transcripts in tumor cell lines and presence in blood samples from patients with prostate cancer. The results of these investigations demonstrate definitively that the identification of the PTI-1 gene is unlikely due to bacterial contamination and/or technical artifacts. Moreover, PTI-1 gene expression may provide an extremely sensitive marker for prostate carcinoma progression as reflected by the presence of prostate carcinoma cells in a patients' bloodstream.

SUMMARY OF THE INVENTION

This invention provides a method for detecting cancer cells in a sample comprising detection of the expression of a Prostate Tumor Inducing Gene in the sample, wherein a positive detection of the expression indicates the presence of cancer cells in the sample.

In an embodiment of this invention, the Prostate Tumor Inducing Gene is PTI-1. In a separate embodiment, the Prostate Tumor Inducing Gene is PTI-2. In another embodiment, the Prostate Tumor Inducing Gene is PTI-3.

In an embodiment, the expression is performed by measuring the level of PTI mRNA. The mRNA is measured by reverse transcription—polymerase chain reaction using at least a pair of appropriate primers. It is well known in the art that once the sequence of the Prostate Tumor Inducing Gene is determined, appropriate pair of primers may be selected.

In an embodiment, at least one of the primers is complementary to either the 5 prime or 3 prime untranslated region. In a further embodiment, the primers are complementary to the 5 prime untranslated region. In a still further embodiment, one of the primers is complementary to the 5 prime untranslated region and the other primer is complementary to the coding region. In another embodiment, the primers are complementary to the 3 prime untranslated region. In separate embodiment, one of the primers is complementary to the 3 prime untranslated region and the other primer is complementary to the coding region.

This invention also provides the above method, wherein the expression is performed by measuring the level of PTI protein. The level of PTI protein is measured by steps of: a) contacting the sample with antibody capable of specifically recognizing PTI-1 protein under conditions permitting formation of complexes between the PTI-1 protein and the antibody; and b) measuring the complex formed, thereby measuring the level of PTI-1 protein expressed in the cancer cells.

BRIEF DESCRIPTION OF THE FIGURES

FIG. 1A is a schematic diagram of the PTI-1 cDNA structure. The 5' and 3' UTRS are represented by thin lines, and the coding region is represented by a hatched box. The thick line represents the bridge specific probe (BSP) used to analyze the junction region between the 5' UTR and the coding region. Arrow heads indicate the position of PCR and RT-PCR primers.

FIG. 1B depicts sequences of PCR and RT-PCR primers and probes used in Southern blotting analysis.

FIGS. 3A–C: PTI-1 gene expression in human tumor cell lines.

FIG. 3A. A specific RT-PCR product with the expected size is generated by primer pairs BU and BL (see FIG. 1) in human prostate, breast and colon carcinoma cell line total RNAs. This product is not present in CREF-Trans 6 cells, but it is present in CREF-Trans 6:4 NMT cell (nude mouse tumor-derived CREF-Trans 6 cells transfected with LNCaP DNA).

FIG. 3B. This RT-PCR product hybridizes with an oligo-nucleotide probe (DSP) using stringent hybridization conditions. The BSP consists of 10 nt on either side of the junction point between the 5' UTR and the coding region of the PTI-1 gene (see FIG. 1A).

FIG. 3C. The same pattern of expression is detected when the 5' UTR specific primer pair UU and UL are used (see FIG. 1A)

FIG. 4A. Ethidium bromide-stained gel of PCR products generated using PSA (14) and PTI-1 5' UTR (7) specific primers in LNCaP cells diluted with CREF-Trans 6 cells.

FIG. 4B. RT-PCR analysis of PTI-1 expression in blood samples from normal males, normal females and prostate cancer patients with stage D disease. The PCR amplified products generated using a PTI-1 5' UTR primer pair (7) were blotted on nylon membranes and probed with a $^{32}$P-labeled DNA fragment of PTI-1. Specific sample were also analyzed by RT-PCR for expression of either PSA or PSN. N=normal; M=male; F=female; DU-145, human prostate carcinoma cell line; N.T.=not tested; +=expression; −=no expression; top number=patient code; D2 and D3=patients with stage D disease.

DETAILED DESCRIPTION OF THE INVENTION

Figures 1A, 1B:
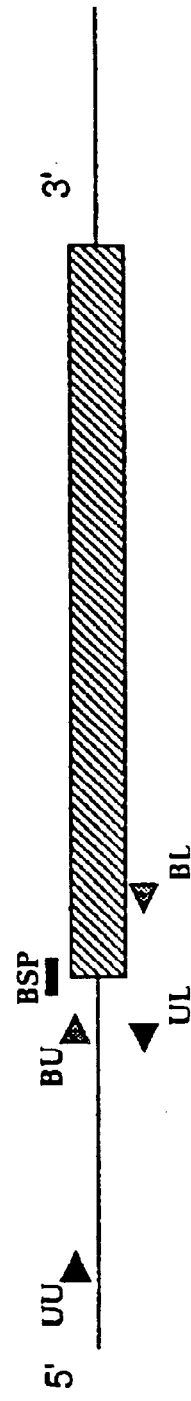
FIGS. 1A–B: Structure of the PTI-1 gene and primer and probe sequences used for analysis.

This invention provides a method for detecting cancer cells in a sample comprising detection of the expression of a Prostate Tumor Inducing Gene in the sample, wherein a positive detection of the expression indicates the presence of cancer cells in the sample. In an embodiment, the cancer cells are carcinoma cells. The cancer cells include but are not limited to prostate cancer cells, breast cancer cells, colon cancer cells and lung cancer cells.

In an embodiment, the sample is a blood sample. In a separate embodiment, the sample is a urine sample. In a further embodiment, the sample is a semen sample.

In an embodiment of this invention, the Prostate Tumor Inducing Gene is PTI-1. In a separate embodiment, the Prostate Tumor Inducing Gene is PTI-2. In another embodiment, the Prostate Tumor Inducing Gene is PTI-3. PTI-1, -2 and -3 are described in U.S. Ser. No. 08/371,377, filed Jan. 11, 1995 now U.S. Pat. No. 5,851,764, and Patent Cooperation Treaty Application No. PCT/US96/00307, filed January 1996.

In an embodiment, the expression is performed by measuring the level of PTI mRNA. The mRNA is measured by reverse transcription—polymerase chain reaction using at least a pair of appropriate primers. It is well known in the art that once the sequence of the Prostate Tumor Inducing Gene is determined, appropriate pair of primers may be selected.

In an embodiment, at least one of the primers is complementary to either the 5 prime or 3 prime untranslated region. In a further embodiment, the primers are complementary to the 5 prime untranslated region. In a still further embodiment, one of the primers is complementary to the 5 prime untranslated region and the other primer is complementary to the coding region. In another embodiment, the primers are complementary to the 3 prime untranslated region. In separate embodiment, one of the primers is complementary to the 3 prime untranslated region and the other primer is complementary to the coding region.

This invention further provides the above method wherein at least one of the primers is selected from a group consisting of

| | |
|---|---|
| 5'GAGTCTGAATAGGGCGACTT3', | (SEQ ID NO:6) |
| 5'AGTCAGTACAGCTAGATGCC3', | (SEQ ID NO:7) |
| 5'ACCCGAGAGGGGAGTGAAATA3', | (SEQ ID NO:1) |
| 5'TGCCGCCATTCCACATTCAGT3', | (SEQ ID NO:2) |
| 5'ATGGGGGTAGAGCACTGAATG3', | (SEQ ID NO:3) |
| 5'AACACCAGCAGCAACAATCAG3' and | (SEQ ID NO:4) |
| 5'AAATTAAGCTATGCAGTCGG3', | (SEQ ID NO:5) |

Since the complete sequence of some Prostate Tumor Inducing gene has been known, other appropriate primer may easily be selected.

This invention also provides the above method, wherein the expression is performed by measuring the level of PTI protein. The level of PTI protein is measured by steps of: a) contacting the sample with antibody capable of specifically recognizing PTI-1 protein under conditions permitting formation of complexes between the PTI-1 protein and the antibody; and b) measuring the complex formed, thereby measuring the level of PTI-1 protein expressed in the cancer cells.

This invention provides a method for detecting cancer cells in a sample comprising steps of: a) isolating mRNA from the sample; b) contacting the isolated mRNA from step a with specific probe capable of recognizing a Prostate Tumor Inducing Gene under conditions permitting formation of a complex between the mRNA and the probe; and c)

detecting of the complex formed wherein a positive detection of the complex indicates the presence of cancer cells in the sample.

This invention provides a method for determining whether a subject has metastatic or late stage prostate cancer comprising steps of: a) obtaining an appropriate sample from the subject; and b) detecting the expression of a Prostate Tumor Inducing Gene in the sample, wherein a positive detection of the expression indicates that the subject has metastatic or late stage prostate cancer. The appropriate sample includes but not limited to a blood, urine and semen sample. The appropriate sample will contain prostate cancer cells such that the expression of Prostate Tumor Inducing gene may be detected.

In an embodiment, the Prostate Tumor Inducing Gene is PTI-1, PTI-2 or PTI-3.

In a specific embodiment of the above method, the expression is performed by measuring the level of PTI-1 mRNA. In a further embodiment, the mRNA is measured by reverse transcription—polymerase chain reaction using at least a pair of appropriate primers. In a still further embodiment, least one of the primers is selected from a group consisting of

| | |
|---|---|
| 5'GAGTCTGAATAGGGCGACTTT3', | (SEQ ID NO:6) |
| 5'GAGTCTGAATAGGGCGACTT3', | (SEQ ID NO:7) |
| 5'ACCCGAGAGGGGAGTGAAATA3', | (SEQ ID NO:1) |
| 5'TGCCGCCATTCCACATTCAGT3', | (SEQ ID NO:2) |
| 5'ATGGGGGTAGAGCACTGAATG3', | (SEQ ID NO:3) |
| 5'AACACCAGCAGCAACAATCAG3' and | (SEQ ID NO:4) |
| 5'AAATTAAGCTATGCAGTCGG3', | (SEQ ID NO:5) |

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Cell Lines.

This study incorporated the following human cell lines: prostate carcinoma (LNCaP, DU-145), breast carcinoma (T47D) and colon carcinoma (SW480). Additional cell types studied include, CREF-Trans 6 cells and nude mouse tumor-derived CREF-Trans 6 cells transfected with LNCaP DNA (CREF-Trans 6:4 NMT) (5). Cells were grown in Dulbecco's modified Eagle's medium (DMEM) supplemented with 5% (rodent cells) or 10% (human cells) fetal bovine serum at 37° C. in a 95% air 5% $CO_2$-humidified incubator. All cell lines used in the present study were tested for mycoplasma contamination using the GenProbe mycoplasma test kit (Gaithersberg, Md.) and found to be mycoplasma free.

Genomic DNA Extraction and PCR.

Human brain and kidneys were frozen in liquid nitrogen, ground into powder, and digested with 100 ug/ml proteinase K at 50° C. overnight, followed by phenol/chloroform extraction and ethanol precipitation (7,8) oligonucleotides were synthesized for PCR amplification corresponding to nt 147 to 167 UU (5' UTR Upper) and nt 550 to 570 UL (5' UTR Lower) of PTI-1 (GenBank, Accession no. L41490). Primer pair UU and UL will generate a 424 bp product. PCR was performed in a 50 ul volume, with 1 ug of brain or kidney genomic DNA, 0.5 uM of each primer (UU and UL), 400 uM dNTPs, 2 mM $Mg^{++}$, and 1 unit of Taq DNA polymerase (GibcoBRL). Forty cycles of amplification were performed with each cycle consisting of 1 min at 95° C., 1 min at 55° C. and 1 min at 72° C. on a programmable thermal cycler (MJ Research). "Hot start" PCR technique was applied. PCR products were analyzed on a 2% agarose gel by ethidium bromide staining.

RNA Isolation from Cultured Cells and RT-PCR.

Total cytoplasmic RNA was isolated from logarithmically growing cell cultures as described previously (9,10) One ug of total RNA extracted from various tumor cell lines was reverse transcribed into cDNA with 150 ng of random primers and 200 units of Superscript II RNase H⁻ Reverse Transcriptase (GibcoBRL) in the presence of 50 mM Tris-HCl (pH 8.3), 75 mM KCl, 3 $mM$ $MgCl_2$, 10 mM DTT and 500 mM dNTPs. The reaction mixture (20 ul) was incubated at 42° C. for 90 min, and terminated by heating at 70° C. for 15 min. Oligonucleotides were synthesized for RT-PCR amplification corresponding to nt 537 to 557 BU (Bridge Upper) and nt 768 to 788 BL (Bridge Lower) of the PTI-1 gene (GenBank, Accession no. L41490). Primer pair BU and BL will generate a 252 bp product. PCR with 2 $\mu$l of the reverse transcription reaction mixture was similar to the genomic DNA protocol with some modifications. Fifteen cycles of amplification were performed in the first round of PCR with primer BU (0.5 uM) alone, and then BL (0.5 uM) primer was added for another 40 cycles of amplification. PCR direct sequencing (New England Biolabs) was performed with [$\gamma$-$^{32}$P]ATP labeled primers following the manufacturer's recommendations.

Southern Blotting Analysis of RT-PCR Products of PTI-1 Gene Transcripts.

Oligonucleotides were synthesized for southern blotting analysis with the BSP (Bridge Specific Probe), 5' AAAT-TAAGCTATGCAGTCGG 3'(SEQ ID NO:5). Ten pmol of the BSP oligonucleotide was incubated with 5 ul [$\gamma$-$^{32}$P]ATP (10 mCi/ml) and 20 units of T4 polynucleotide kinase (GibcoBRL) at 37° C. for 60 min in the presence of 70 mM Tris-HCl (pH 7.6), 10 mM $MgCl_2$, 100 mM KCl and 1 mM $\beta$-mercaptoethanol. The reaction was terminated by heating at 70° C. for 10 min, and labeled oligonucleotide probe was purified by ethanol precipitation. RT-PCR products amplified by the BU and BL primer pair were transferred onto nylon membrane (Hybond film, Amersham) according to standard capillary blotting protocols. After fixation at 80° C. for 2 hr, the membrane was incubated at 56° C. overnight in the presence of 1% SDS, 1 M NaCl and 100 ug/ml sonicated salmon sperm DNA. Hybridization was performed the next day by incubating with 1% SDS, IM NaCl and labeled probe at 56° C. overnight. The membrane was washed twice with 100 ml 2 × SSC at room temperature for 5 min each, once with 200 ml 2 × SSC, 1% SDS at 56° C. for 30 min, and once with 200 ml 0.1% SSC at room temperature. The blot was exposed with Kodak X-OMAT film for 30 min at room temperature.

Determination of PCR Sensitivity.

RNA was isolated from LNCaP cells and from mixtures of LNCaP and CREF-Trans 6 cells ranging from 1:1000 to 1:100000000 as previously described (9,10). PCR was performed using PTI-1 5' UTR specific primers (5'-GAGTCTGAATAGGGCGACTT-3' (SEQ ID NO:6) and 5'-AGTCAGTACAGCTAGATGCC-3'(SEQ ID NO:7)) (7) and PSA specific primers (5'-TACCCACTGCATCAGGAACA-3'(SEQ ID NO: 8) and 5'-CCTTGAAGCACACCATTACA-3'(SEQ ID NO: 9)) (14). The CREF-Trans 6 cell line was chosen to dilute LNCaP cells because this cell line does not express PTI-1 or PSA (7,8).

Patient Blood Samples, RNA Processing and PCR.

Blood samples used in this study were obtained from patients at Columbia-Presbyterian Hospital and Mount Sinai Medical Center. Specimens were obtained with informed consent of each patient using protocols approved by the Institutional Review Boards of each respective hospital. Sample analysis included blood samples from 9 patients with stage D disease (3 with D2 and 6 with D3), 12 patients with localized cancer of the prostate, 3 healthy males and 3 healthy females. Venous blood (5 cc) was collected in ethylenediaminetetracetic acid (EDTA) treated collection tubes, placed on ice and processed within 3 hr of phlebotomy (11). Samples were diluted in an equal volume of PBS and layered onto 8cc of Ficoll-Plaque. The samples were centrifuged at 400 × gravity for 30 min and the buffy coat cells were recovered. The cells were washed in PBS before RNA extraction. RNA was extracted as previously described (11,14) using a modified guanidinium thiocyanate/phenol/chloroform extraction technique (11) using the RNazole B reagent. Selected samples were analyzed for PSA and PSM expression by PCR using previously described techniques and primers (7,10,14). PTI-1 expression was evaluated using the same 5' UTR primer pair used for determining PCR sensitivity (7). Positive and negative PTI-1 expression was also confirmed in a subset of samples using PCR with the UU and UL and the BU and BL primer pairs.

Experimental Results

The 5' UTR Sequence of the PTI-1 Gene is Present in the Human Genome.

If PTI-1 is truly an etiologic agent in human prostate cancer, then this gene or related DNA sequences must be a component of human genetic material. Demonstration that the 5' UTR of PTI-1, which displays a strikingly high degree of homology with prokaryotic ribosomal RNA sequences, is indeed present in the human genome was deemed a priority for future mechanistic studies of the PTI-1 gene. Moreover, this information is required before and irrespective of the mechanism by which activation of this sequence occurs during cancer development.

Figure 2:
FIG. 2: The 5' UTR sequence of the PTI-1 gene is present in the human genome. One µg of human cerebellum genomic DNA is amplified with primer pairs UU (SEQ ID NO:1) and UL (SEQ ID NO:2) (see FIG. 1). A specific PCR product with the anticipated size of 424 bp is generated, which is not affected by RNaseA treatment. This product is not generated following removal of either one of the primers, DNA template, or Taq polymerase. MW, molecular weight marker, is 100 bp DNA ladder (GibcoBRL).

As shown in FIG. 2, primer pair UU and UL (representing sequences in the 5' UTR of PTI-1) generated a specific PCR product with the expected size (424 bp) from human brain genomic DNA. The size of the PCR product from genomic DNA (FIG. 2, Lanes 1 and 2) is the same size as that of the PTI-1 cDNA suggesting that it is an intron free region. It is well documented that both prokaryotic and eukaryotic ribosomal RNA genes are without introns and the findings reported here are consistent with this conclusion (12). RNase digestion of the template did not affect the detection of this product. The amplification of this product also required the simultaneous presence of all the following components in the PCR reaction mixture: Taq polymerase, both primers and the template DNAs (FIG. 2). Similar experimental results occur when human kidney genomic DNA is substituted for brain genomic DNA (data not shown).

Although the present studies cannot rule out definitively the possibility of a minute quantity of bacterial DNA in the genomic DNA preparations, thereby generating false positive results, it is recognized that the probability of Mycoplasma contamination is less likely in tissue samples than in cell cultures (13). The possibility that mycoplasma contamination is present in the experimental reagents is not likely at the level of sensitivity currently used to detect PTI-1 in experimental DNA samples. These results support the conclusion that the 5' UTR sequence of the PTI-1 gene is actually a normal component of the human genome.

Detection of Junction Sequences Located Between the 5' UTR and the EF-1α Coding Region of the PTI-1 Gene in Total RNA from Tumor Cell Lines.

It is hypothesized that even if there is Mycoplasma or related bacterial contamination in the cell cultures studied, this contamination alone could not explain the presence of both prokaryotic ribosomal RNA sequences and human EF-1a sequences contiguous on the same RNA molecule. Thus, if such a junction point can be demonstrated to exist in total RNA, it is unlikely that the identification of PTI-1 gene was due to an experimental artifact. As shown in FIG. 3 (panel A), primer pair BU (consisting of sequences within the 5' UTR of PTI-1) and BL (consisting of sequences within the EF-1a region of PTI-1) generates an RT-PCR product with the expected size (252 bp) in total RNAs from CREF-Trans 6:4 NMT (nude mouse tumor-derived CREF-Trans 6 clone transfected with LNCaP HMW DNA), T47D (human breast carcinoma), SW480 (human colon carcinoma) and LNCaP and DU-145 (human prostate carcinoma) cells. This PCR product was not detected in RNAs extracted from CREF-Trans 6 cells. This expression pattern is identical to that previously reported using Northern blotting analysis and probing with a PTI-1 5' UTR-specific probe (7). As shown in panel B, this PCR product also hybridizes with a PTI-1 cDNA specific oligonucleotide BSP. The BSP consists of 20 nucleotides, with 10 nucleotides on either side of the junction point between the 5' UTR and the coding region of the PTI-1 cDNA (FIG. 1). The highly stringent hybridization and washing conditions (see Materials and Methods) used in Southern blotting analysis demonstrates that this PCR product contains the PTI-1 cDNA sequences, specifically the sequence surrounding the junction point between the 5' UTR and coding region of the PTI-1 gene. This conclusion was further supported by direct sequencing of one of the PCR products obtained from the tumor-derived CREF Trans 6:4 NMT cell line (data not shown), which documents that it consists of both prokaryotic ribosomal-like RNA sequences and human EF-la sequences. These sequences were the same as those published previously for the PTI-1 gene (7).

It was also important to rule out the possibility that the PTI-1 plasmid might be a source of potential contamination generating artifactual results. The PTI-1 gene was initially identified as a 1.8 Kb insert from an LNCaP cDNA library. Subsequently, the remaining 215 bp at the 5' end was obtained by the RACE procedure (7). Since the missing region of PTI-1 was located in the 5' UTR, a full-length PTI-1 cDNA was never generated. Therefore, any PCR or RT-PCR products produced with primers constructed from the first 215 bp and remaining 415 bp regions of the 5' UTR of PTI-1 could not be derived from a plasmid template, but could only result from RNA or genomic DNA. As shown in FIG. 3 (panel C), primer pair UU (located inside the first 215 bp region that is missing in the PTI-1 cDNA clone) and UL (designed within the 5' UTR of PTI-1 that is present in the PTI-1 cDNA clone) permitted the amplification of the 5' UTR sequences of PTI-1 from the same total RNAs of tumor cell lines that were positive for the bridge region. Moreover, the pattern of expression of this sequence is identical to that of the junction sequences of the PTI-1 gene (FIG. 3 A and B).

These results document that the PTI-1 gene is an authentic putative human oncogene that is expressed in specific human tumor cell lines derived from appropriately transfected CREF-Trans 6 (CREF-Trans 6:4 NMT) and prostate and additional human carcinomas.

Expression of the PTI-1 Gene in Prostate Carcinoma Patient Blood Samples.

Figure 4A:
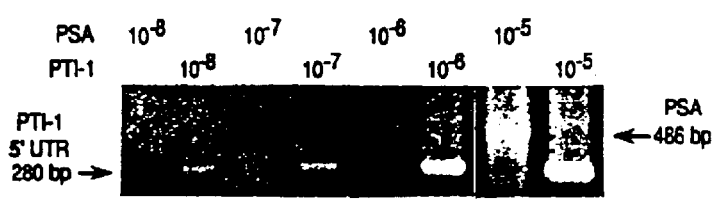
FIGS. 4A–B: Sensitivity of PTI-1 in detecting prostate carcinoma cells in diluted cell culture samples and in patient blood samples.

To determine the sensitivity of PTI-1 as a gene-based marker for detecting prostate carcinoma cells, PTI-1 expressing LNCaP cells were serially diluted with non-PTI-1 expressing CREF-Trans 6 cells, total RNA was isolated and samples were compared by RT-PCR for PTI-1 expression (FIG. 4A). Using primers designed in the unique 5' UTR region of PTI-1, a positive PTI-1 specific amplified fragment (280 bp) was detected when 1 LNCaP cell was diluted in 108 CREF-Trans 6 cells. In contrast, when primer sequences corresponding to PSA were employed in the amplification, a weaker signal (corresponding to a 486 bp fragment) was obtained that represented 1 LNCaP cell diluted in $10^6$ CREF-Trans 6 cells. The efficiency of detection of PSM (14) in serially diluted cells using a single pair of PSM-specific primers (generating a 647 bp fragment) was even less sensitive than PSA detecting 1 prostate carcinoma cell diluted in $10^5$ CREF-Trans 6 cells (data not shown). These results demonstrate that RT-PCR of PTI-1 is currently the most sensitive detector of human prostate carcinoma cells available, significantly exceeding the sensitivity of PSA and PSM.

Figure 4B:
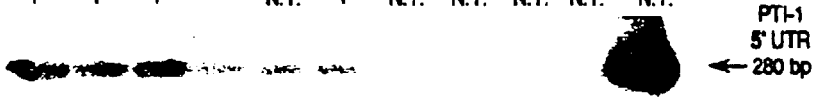
Figure 5:
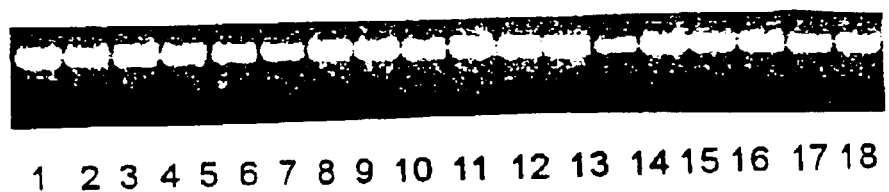
FIG. 5: RT-PCR of GAPDH, samples are treated according to the description in the Second Series of Experiment. Both GAPDH and the Bridge region RT-PCT involved one round of amplification. Two round of amplification (30 cycles/round) was required to achieve a signal with the 5' UTR primers.
Figure 5:
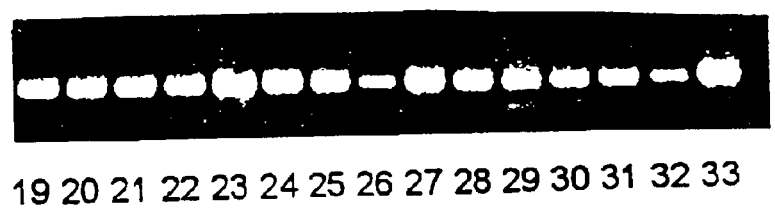
Figure 6:
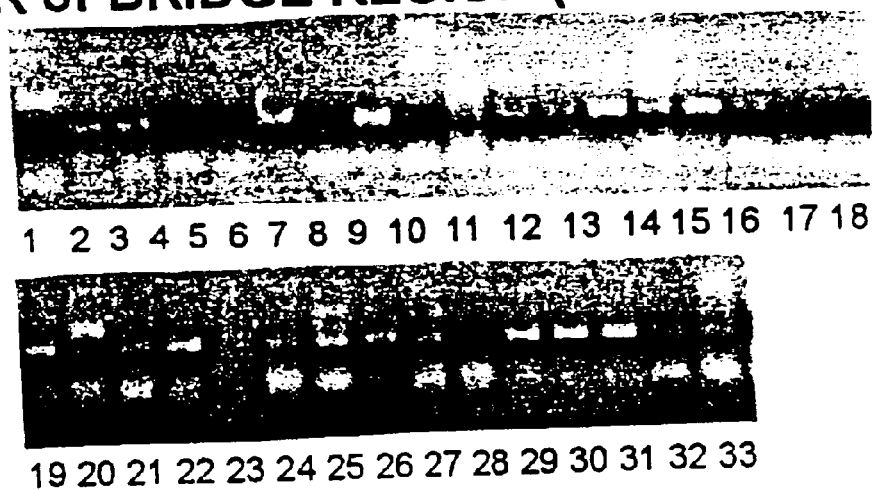
FIG. 6 RT-PCR of Bridge region (BU and BL)
Figure 7:
FIG. 7 RT-PCR of 5'UTR
Figure 7:

The exquisite sensitivity of PTI-1 in detecting prostate cancer cells in diluted samples (FIG. 4A) suggested that monitoring PTI-1 transcripts might also prove useful as a direct screening test for the detection of prostate carcinoma cells in the circulatory system of prostate cancer patients. To determine if this assumption was correct, RT-PCR was performed using primers specific for the 5' UTR of PTI-1 with RNAs isolated from blood samples confirmed as positive or negative for PSA and/or PSM expression (FIG. 4B). PTI-1 was able to detect carcinoma cells in samples found to be positive for both PSA and PSM as well as samples found to be positive for only one of these two markers. In contrast, 6 confirmed negative samples from volunteer females and males and 4 patients with prostate cancer that had not spread past the margin of the prostate gland (also found negative for PSA and/or PSM) were negative for PTI-1 expression (total of 18 samples: 8 of 8 confirmed positives, 10 of 10 confirmed negatives) (FIG. 4B and unpublished data).

A second test of PTI-1 involved a double-blind study using 9 random RNAs isolated from blood specimens. These samples were analyzed for PSA and PTI-1 expression by RT-PCR using PSA-specific primers (11) and the primer pair UU and UL (within the 5' UTR of PTI-1), respectively. Of these 9 samples, two were found to be positive for PTI-1 transcripts. These two samples were also positive for PTI-1 when using the BU and BL primer pair. One patient determined to have metastatic prostate cancer, was positive for PTI-1 expression, but negative for PSA expression. However, the other PTI-1 positive patient was assumed by pathology to have localized cancer in the prostate gland and this patient's blood sample was also negative for RT-PCR of PSA. In the remaining 7 patients, 7 were confirmed as having non-metastatic prostate cancer and they were all negative for PTI-1 expression, whereas 5 of 7 were negative and 2 were positive for PSA expression. The only patient who was suspicious for metastatic prostate cancer based on very high serum PSA protein levels, was negative by RT-PCR for expression of both PTI-1 and PSA.

Taken together the studies described above indicate that 9 of 10 (90% sensitivity) prostate cancer patients with confirmed metastatic disease were positive for PTI-1 expression by RT-PCR, whereas only 4 of 9 (44% sensitivity) blood samples from the same patients with metastatic disease expressed PSA. Moreover, only 1 of 13 (~8% potential false positive) patients without detectable signs of prostate carcinoma spreading from the prostate gland were positive for PTI-1, whereas 2 of 10 (20% potential false positive) patients in the same group were positive for PSA. Although further studies are needed with a larger number of patient samples, including patients with and without confirmed metastatic prostate cancer, the present studies provide compelling evidence suggesting that RT-PCR of PTI-1 should prove useful as a sensitive methodology for monitoring extraprostatic disease in patients prior to surgery, staging prostate cancer and evaluating patients' response to chemotherapy and radiation therapy.

Experimental Discussion

The ability to accurately monitor the aggressiveness of human prostate cancer is a priority for defining the appropriate means of therapeutically intervening in the progression of this disease. Recent studies document that the identification of blood-borne PSA-expressing cells by RT-PCR can be achieved in patients with localized as well as metastatic prostate cancer and that this detection provides a dependable marker for predicting local invasion of a prostate tumor preceding surgical procedures (11,14,15). PSA, a 34 kDa glycoprotein, is a prostate-associated serine protease with predominant expression by prostate epithelial cells, the cells most often associated with prostatic oncogenesis (16,17). Recently, assays used to monitor this protein in the blood have changed the management of prostate cancer patients by permitting the early detection of prostate tumors as well as by providing a more efficient means to follow the progression of this disease. The specificity of PSA for prostate cells has permitted the development of an RT-PCR based assay that can detect as few as 1 PSA-synthesizing cell in 106 non-PSA expressing blood cells (11,14,15). A further enhancement of the PSA assay involves the addition of digoxigenin-modified nucleotide to the PCR reaction (9,13). A Southern blot made from such electrophoreses reaction products can then be analyzed by sensitive immunostaining techniques that greatly enhance the detection of the specific PSA-derived cDNA product. When this enhanced assay was previously applied to peripheral blood specimens taken from prostate cancer patients with confirmed metastases, it was positive for the majority (77.7w) of patients in this category that were studied (9,13). PTI-1 is not expressed in normal prostate or BPH, but PTI-1 expression is apparent in both PSA-positive hormone-sensitive, LNCaP, and PSA-negative hormone-refractive, DU-145, human prostate carcinoma cells (7). The current study demonstrates a $\geq 100$-fold increase in the sensitivity of RT-PCR of PTI-1 versus PSA and PSM in detecting prostate cancer cells. Moreover, PTI-1 RT-PCR resulted in an ~90% sensitivity in detecting patients with metastatic prostate cancer versus an ~44% sensitivity with the same patient samples using RT-PCR with PSA. In these contexts, an RT-PCR-based assay using PTI-1 may permit the detection of prostate cancer cells in the circulation that would not be detected using RT-PCR with PSA or PSM. In addition, the specificity of PCTA-1 for prostate carcinoma versus normal prostate or BPH eliminates the possibility of generating false positives that could occur using RT-PCR of PSA or PSM.

Important questions that were experimentally addressed include the nature of the 5' UTR region of PTI-1 that displays homology to bacterial ribosomal 23S RNA and the genuineness of the PTI-1 gene (7). The PTI-1 gene was cloned from an LNCaP human prostate cancer cDNA library using a 214 bp fragment detected by differential RNA display in LNCaP DNA transfected tumor-derived CREF- Trans 6 cells (7). Sequence analyses confirm that the 214 bp sequence with homology to prokaryotic ribosomal RNA is located within the 5' UTR of the PTI-1 gene (7) Although all of the cell lines used in the original study were tested using the GenProbe mycoplasma test kit and found to be free of mycoplasma contamination, it is still possible that the PTI-1 gene arose from a cloning artifact generated by a low level of undetected bacterial contamination present in the CREF-Trans 6:4 NMT or LNCaP cell lines. Several lines of evidence are presently provided that argue against this possibility and validate the authenticity of the PTI-1 gene. Using PCR-based approaches with genomic DNAs isolated from human brain and kidney, the presence of the prokaryotic ribosomal RNA homologous sequences in the human genome is doucmented by this study. Using an RT-PCR-based strategy with primers corresponding to the 5' UTR and EF-1α coding region of PTI-1, an appropriate junction sequence is amplified from total RNA from CREF Trans 6:4 NMT cells, various human tumor cell lines and blood samples from patients with confirmed metastatic prostate cancer. Even if the tissue samples and cell lines contained mycoplasma or related bacterial contamination, these adventitious organisms alone would not be capable of generating the unique junction sequence in a population of total cytoplasmic RNAS. The ability to detect such a junction sequence in total RNAs from specific cancer cells provides compelling evidence for the authenticity of the PTI-1 gene and its' encoded message.

The present study raises a number of important issues that require resolution in order to define the role of PTI-1 in human cancer etiology and evolution. Documentation of the presence of the 5' UTR mycoplasma homology region in the human genome forces one to examine the potential origin of such prokaryotic gene sequences in the eukaryotic genome. Although no mechanism is provided, a recent study suggests a potential relationship between persistent chronic infection with mycoplasmas and malignant transformation (18). Unlike retroviruses and DNA tumor viruses which can incorporate their genetic material into the host genome, no evidence is currently available indicating that mycoplasma gene sequences can integrate into the human genome as part of their infectious cycle. However, it is possible that Mycoplasma, or more likely one of its ancestors, may randomly insert its genetic material into human or one of its ancestor's genome. This integration may occur by a mechanism that is similar to that by which foreign gene sequences insert into the genome of transgenic animals. The presence of sequences that are highly homologous to prokaryotic genes in the human genome has been previously reported, although the functions of these sequences are not known (19). It is very tempting to speculate that, based on the high degree of homology between the 5' UTR of PTI-1 and mycoplasma gene sequences, such an event may have occurred recently in evolution, thereby generating the PTI-1 gene.

Additional important issues are the mechanism by which PTI-1 expression is activated in human tumor cells and the role of PTI-1 in mediating the cancer phenotype. Differential expression of PTI-1 in cancer cells may occur by activation of transcription from an upstream promoter from the EF-la or another target gene, resulting in transcription of the 5' UTR and EF-1α region of PTI-1. Alternatively, gene activation could result from genome rearrangement, including gene deletion, inversion and translocation, which are common occurrences in many cancers (20,21). Elucidation of the genomic structure, including the promoter region, of PTI-1 is necessary to shed light on this question and to define the molecular basis for the differential expression of PTI-1 in human prostate, and additional, cancers versus normal cells.

Further studies are also necessary to determine the functional relevance of PTI-1 expression in determining the cancer phenotype. If PTI-1 expression is shown to be causally related to cancer development or progression, then this gene could serve as a potential target for inhibiting the neoplastic process.

Second Series of Experiments

Bloods were screened for the presence of PTI-1 using a previously described protocol (Sun, et al. Cancer Research 57:18–23, 1997). Briefly, total RNA was reverse transcribed into cDNA with 150 ng of random primers and 200 U of Superscript II RNAase H' (Life Technologies) in the presence of 50 mM Tris-HCL pH8.3, 75 mM KCI, 3 mM MgCI2, 10 mM DTT, and 500 uM deoxynucleotide triphosphates. The reaction mixture (20 ul) was incubated at 42C for 90 minutes and terminated by heating at 70C for 15 minutes oligonucleotides were synthesized for RT-PCR amplification according to sequence of the PTI-1 gene (GenBank accession no. L41490). The following primer pairs were used:

```
PrimerUU (5'UTR Upper)
5'ACCCGAGAGGGGAGTGAAATA3'      (SEQ ID NO:1)

PrimerUL (5'UTR Lower)
5'TGCCGCCATTCCACATTCAGT3'      (SEQ ID NO:2)

PrimerBU (Bridge Upper)
5'ATGGGGGTAGAGCACTGAATG3'      (SEQ ID NO:3)

PrimerBL (Bridge Lower)
5'AACACCAGCAGCAACAATCAG3'      (SEQ ID NO:4)

Oligonualeotide BSP (Bridge Specific Probe)
5'AAATTAAGCTATGCAGTCGG3'       (SEQ ID NO:5)
```

Experimental Results

All mRNAs were screened for degradation by electrophoresis (not shown) and for the presence of the housekeeping gene, GAPDH, by RT-PCR (FIG. 1). Amplification with the BU and BL primers is shown in FIG. 2. As can be seen, a large number of blood RNAs were positive for the presence of the bridge region. A sample from an individual with no evidence of cancer had a very light band. This gel was blotted and subsequently probed with a 20 mer bridge specific primer (BSP). As can be seen in Table 1, 14 of 33 samples were positive.

TABLE 1

Blood samples positive for the bridge (BU and BL) and the bridge specific (BSP) primers

| SAMPLE | BSP | BU/BL |
|---|---|---|
| 1 | Neg | Neg |
| 2 | + | Pos |
| 3 | Neg | Pos |
| 4 | Neg | Neg |
| 5 | Neg | Neg |
| 6 | +++ | Pos |
| 7 | Neg | +/− |
| 8 | +++ | Pos |
| 9 | Neg | Neg |
| 10 | Neg | Pos |
| 11 | + | Pos |
| 12 | Neg | Pos |
| 13 | +++ | Pos |
| 14 | Neg | Pos |
| 15 | +++ | Pos |
| 16 | Neg | Pos |
| 17 | Neg | Neg |
| 18 | Neg | Neg |
| 19 | +++ | Pos |

TABLE 1-continued

Blood samples positive for the bridge (BU and BL)
and the bridge specific (BSP) primers

| SAMPLE | BSP | BU/BL |
|---|---|---|
| 20 | Neg | Pos |
| 21 | Neg | Pos |
| 22 | +++ | Pos |
| 23 | Neg | Neg |
| 24 | Neg | Pos |
| 25 | Neg | Pos |
| 26 | ++ | Pos |
| 27 | Neg | Pos |
| 28 | Neg | Neg |
| 29 | ++ | Pos |
| 30 | +++ | Pos |
| 31 | +++ | Pos |
| 32 | + | +/− |
| 33 Normal Sample | Neg | +/− |

The normal blood sample (#33) was negative for the BSP. Additional screening of the blood samples was done using the 5' UTR primers UU and UL. It required two rounds of amplification to visualize the bands. As can be seen, 4 of 33 samples had a band in the appropriate bp region (FIG. 3). Two additional samples had a band slightly higher and slightly lower than the expected molecular weight. The normal blood sample was negative for the 5' UTR.

Experimental Discussion

The results of these experiments confirm the earlier utility of PTI-1 as a diagnostic for late stage prostate cancer All of the positive samples (using the BSP and the 5' UTR) had previously been diagnosed as having late stage or metastatic disease. Interestingly, two bands were evident using the 5' UTR primers that differed from the expected molecular weight for PTI-1. Since this gene is a member of a large family of related sequences, it is possible that other PTIs may have diagnostic utility for cancer detection.

References

1. Epstein, J. I., Pizov, G., and Walsch, P. C. Correlation of pathologic findings with progression after radical retropubic prostatectomy. Cancer, 71: 3582–3593, 1993.
2. Mukamel, E., Hanna, J., and deKernion, J. B. Pitfalls in preoperative staging in prostate cancer. Urol., 30: 318–323, 1987.
3. Salo, J. O., Kivisaari, L., Rannikko, S., and Lehtonen, T. J. Computerized tomography and transrectal ultrasound in the assessment of local extension of prostatic cancer before radical retropubic prostatectomy. J. Urol., 137: 435–438, 1987.
4. Lu-Yao, G. L., McLerran, D., Wasson, J., and Wennberg, J. E. An assessment of radical prostatectomy. Time trends, geographic variation and outcomes. The Prostate Patient Outcomes Research Team. JAMA, 269: 2633–2636, 1993.
5. Su, Z.-z., Olsson, C. A., Zimmer, S. G., and Fisher, P. B. Transfer of a dominant-acting tumor-inducing oncogene from human prostatic carcinoma cells to cloned rat embryo fibroblast cells by DNA-transfection. Anticancer Res., 12: 297–304, 1992.
6. Liang, R., and Pardee, A. B. Differential display of eukaryotic messenger RNA by means of the polymerase chain reaction. Science (Washington D.C.), 257: 967–997, 1992.
7. Shen, R., Su, Z.-z., Olsson, C. A., and Fisher, P. B. Identification of the human prostatic carcinoma oncogene PTI-1 by rapid expression cloning and differential RNA display. Proc. Natl. Acad. Sci. U.S.A., 92: 6778–6782, 1995.
8. Su, Z. -z., Lin, J., Shen, R., Fisher, P. E., Goldstein, N. I., and Fisher, P. B. Surface-epitope masking and expression cloning identifies the human prostate carcinoma tumor antigen gene PCTA-1 a member of the galectin gene family. Proc. Natl. Acad. Sci. U.S.A., 93: 7252–7257, 1996.
9. Jiang, H., and Fisher, P.B. Use of a sensitive and efficient subtraction hybridization protocol for the identification of genes differentially regulated during the induction of differentiation in human melanoma cells. Mol. Cell. Different., 1 (3): 285–299, 1993.
10. Jiang, H., Lin, J., Su, Z. Z., Herlyn, M., Kerbel, R. S., Weissman, B. E., Welch, D. R., and Fisher, P. B. The melanoma differentiation-associated gene mda-6, which encodes the cyclin-dependent kinase inhibitor p21, is differentially expressed during growth, differentiation and progression in human melanoma cells. Oncogene, 10: 1855–1864, 1995.
11. Katz, A. E., Olsson, C. A., Raffo, A. J., Cama, C., Perlman, H., Seaman, E., O'Toole, K. M., McMahon, D., Benson, M. C., and Buttyan, R. Molecular staging of prostate cancer with the use of an enhanced reverse transcriptase-PCR assay. Urol., 43: 765–775, 1994.
12. Noller, H. F. Ribosomal RNA and translation. Annu. Rev. Biochem., 60:191–227,1991.
13. Chastel, C. Links and interactions between mycoplasmas and viruses: past confusions and present realities. Arch. Virol., 140: 811–826, 1995.
14. Israeli, R. S., Miller, W. H., Jr., Su, S. L., Powell, T., Fair, W. R., Samadi, S. D., Huryk, R. F., DeBlasio, A., Edwards, E. T., Wise, G. J., and Heston, W. D. W. Sensitive nested reverse transcription polymerase chain reaction detection of circulating prostatic tumor cells: comparison of prostate-specific membrane antigen and prostate-specific antigen-based assays. Cancer Res., 54: 6306–6310, 1994.
15. Cama, C., Olsson, C. A., Raffo, A. J., Perlman, H., Buttyan, R., O'Toole, K., McMahon, D., Benson, M. C., and Katz, A. E. Molecular staging of prostate cancer II. A comparison of the application of an enhanced reverse transcriptase polymerase chain reaction assay for prostate specific antigen versus prostate specific membrane antigen. J. Urol., 153: 1373–1378, 1995.
16. Wang, M. C., Valenzuela, L. A., Murphy, G. P., and Chu, T. M. Purification of a human prostate specific antigen. Invest. Urol., 17: 159–163, 1979.
17. Watt, K. W. K., Lee, P.-J., Timkulu, M., Chan, W.-P., and Loor, R. Human prostate-specific antigen: structural and functional similarity with serine proteases. Proc. Natl. Acad. Sci. U.S.A., 83: 3166–3170, 1986.
18. Tsai, S., Wear, D. J., Shih, J. W. -K., and Lo S. -C., Mycoplasmas and oncogenesis: persistent infection and multistage malignant transformation. Proc. Natl. Acad. Sci. U. S. A., 92: 10197–10201, 1995.
19. Veronese, M. L., Bullrich, F., Negrini, M., and Croce, C. M. The t(6;16)(p21;q22) chromosome translocation in the LNCaP prostate carcinoma cell line results in tpc/hpr fusion gene. Cancer Res., 56: 728–732, 1996.
20. Shima, Z. A., Le Beau, M. M., McKeithan, T. W., Minowada, J., Showe, L. C., Mak, T. W., Minden, M. D., Rowley, J. D., and Diaz, M. 0. Gene encoding the a chain of the T-cell receptor is moved immediately downstream of c-myc in a chromosomal 8;14 translocation in a cell line from a human T-cell leukemia. Proc. Natl. Acad. Sci. U.S.A., 83: 3439–3443, 1986.
21. Crozat, A., Aman, P., Mandahl, N., and Ron, D. Fusion of CHOP to a novel RNA-binding protein in human myxoid liposarcoma. Nature, 363: 640–641, 1993.

What is claimed is:

1. A method for detecting cancer cells in a sample comprising detection of the expression of a Prostate Tumor Inducing Gene-1 in the sample, comprising the steps of:
   (a) preparing RNA from the sample;
   (b) performing reverse transcription polymerase chain reaction under conditions that permit copies of Prostate Tumor Inducing Gene-1 nucleic acid to be produced, using primers specific for said Prostate Tumor Inducing Gene-2; and
   (c) determining whether a detectable amount of product is produced by the reverse transcription-polymerase chain reaction:
wherein a detectable amount of product constitutes a positive detection of expression, a positive detection of expression indicates the presence of cancer cells in the sample, and said Prostate Tumor Inducing Gene-1 is SEQ ID NO:16 of U.S. Pat. No. 5,851,764.

2. The method of claim 1, wherein the cancer cells are carcinoma cells.

3. The method of claim 1, wherein the cancer cells are prostate cancer cells, breast cancer cells, colon cancer cells or lung cancer cells.

4. The method of claim 1, wherein the sample is a blood, urine or semen sample.

5. The method of claim 1, wherein the expression is performed by measuring the level of Prostate Tumor Inducing Gene-1 mRNA.

6. The method of claim 1, wherein at least one of the primers is complementary to either the 5 prime untranslated region of the Prostate Tumor Inducing Gene-1.

7. The method of claim 6, wherein one of the primers is complementary to the 5 prime untranslated region and the other primer is complementary to the coding region.

8. The method of claim 6, wherein one of the primers is complementary to the 3 prime untranslated region and the other primer is complementary to the coding region.

9. The method of claim 5, wherein at least one of the primers is selected from a group consisting of:

| | |
|---|---|
| 5'GAGTCTGAATAGGGCGACTT3', | (SEQ ID NO:6) |
| 5'AGTCAGTACAGCTAGATGCC3', | (SEQ ID NO:7) |
| 5'ACCCGAGAGGGGAGTGAAATA3', | (SEQ ID NO:1) |
| 5'TGCCGCCATTCCACATTCAGT3', | (SEQ ID NO:2) |
| 5'ATGGGGGTAGAGCACTGAATG3', | (SEQ ID NO:3) |
| 5'AACACCAGCAGCAACAATCAG3' and | (SEQ ID NO:4) |
| 5'AAATTAAGCTATGCAGTCGG3'. | (SEQ ID NO:5). |

10. A method for determining whether a subject has metastatic or late stage prostate cancer comprising the steps of:
   (a) obtaining an appropriate sample from the subject;
   (b) preparing RNA from the sample;
   (c) performing reverse transcription-polymerase chain reaction under conditions that permit copies of Prostate Tumor Inducing Gene-1 nucleic acid to be produced, using primers specific for the Prostate Tumor Inducing Gene-1; and
   (d) determining whether a detectable amount of Prostate Tumor Inducing Gene-1 product is produced by the reverse transcription-polymerase chain reaction;
wherein a detectable amount of product constitutes a positive detection of expression, a positive detection of expression indicates that the subject has metastatic or late stage prostate cancer, and said Prostate Tumor Inducing Gene-1 is SEQ ID NO:16 of U.S. Pat. No. 5,851,764.

11. The method of claim 10, wherein the sample is a blood, urine or semen sample.

12. The method of claim 10, wherein the expression is performed by measuring the level of PTI-1 mRNA.

13. The method of claim 12, wherein at least one of the primers is selected from the group consisting of:

5'GAGTCTGAATAGGGCGACTT3', (SEQ ID NO:6)

5'AGTCAGTACAGCTAGATGCC3', (SEQ ID NO:7)

5'ACCCGAGAGGGGAGTGAAATA3', (SEQ ID NO:1)

5'TGCCGCCATTCCACATTCAGT3', (SEQ ID NO:2)

5'ATGGGGGTAGAGCACTGAATG3', (SEQ ID NO:3)

5'AACACCAGCAGCAACAATCAG3' and (SEQ ID NO:4)

5'AAATTAAGCTATGCAGTCGG3'. (SEQ ID NO:5).

* * * * *

UNITED STATES PATENT AND TRADEMARK OFFICE
CERTIFICATE OF CORRECTION

PATENT NO. : 6,869,760 B2
APPLICATION NO. : 09/263981
DATED : March 22, 2005
INVENTOR(S) : Paul B. Fisher It is certified that error appears in the above-identified patent and that said Letters Patent is hereby corrected as shown below:

In the Claims:
Col. 17, line 41: "Gene-2" should read -- Gene-1 --
Col. 17, line 60: "the 5 prime untranslated" should read -- the 5 prime or 3 prime untranslated --
Col. 18, line 35: "5' GAGTCTGAATAGGGCGACTT3' , (SEQ ID NO:6)" should read -- 5' GAGTCTGAATAGGGCGACTT3' (SEQ ID NO:6), --
Col. 18, line 37: "5' AGTCAGTACAGCTAGATGCC3' , (SEQ ID NO:7)" should read -- 5' AGTCAGTACAGCTAGATGCC3' (SEQ ID NO:7), --
Col. 18, line 39: "5' ACCCGAGAGGGGAGTGAAATA3' , (SEQ ID NO:1)" should read -- 5' ACCCGAGAGGGGAGTGAAATA3' (SEQ ID NO:1), --
Col. 18, line 40: "5' TGCCGCCATTCCACATTCAGT3' , (SEQ ID NO:2)" should read -- 5' TGCCGCCATTCCACATTCAGT3' (SEQ ID NO:2), --
Col. 18, line 42: "5' ATGGGGGTAGAGCACTGAATG3' , (SEQ ID NO:3)" should read -- 5' ATGGGGGTAGAGCACTGAATG3' (SEQ ID NO:3), --
Col. 18, line 44: "5' AACACCAGCAGCAACAATCAG3' , (SEQ ID N0:4)" should read -- 5' AACACCAGCAGCAACAATCAG3' (SEQ ID NO:4), and --
Col. 18, line 45: "5' AAATTAAGCTATGCAGTCGG3' . (SEQ ID NO:5)" should read -- 5' AAATTAAGCTATGCAGTCGG3' (SEQ ID NO:5). --
Col. 19, line 5: "5' GAGTCTGAATAGGGCGACTT3' , (SEQ ID NO:6)" should read -- 5' GAGTCTGAATAGGGCGACTT3' (SEQ ID NO:6), --
Col. 19, line 6: "5' AGTCAGTACAGCTAGATGCC3' , (SEQ ID NO:7)" should read -- 5' AGTCAGTACAGCTAGATGCC3' (SEQ ID NO:7), --
Col. 19, line 7: "5' ACCCGAGAGGGGAGTGAAATA3' , (SEQ ID NO:1)" should read -- 5'A000GAGAGGGGAGTGAAATA3' (SEQ ID NO:1), --
Col. 19, line 8: "5' TGCCGCCATTCCACATTCAGT3' , (SEQ ID N0:2)" should read -- 5' TGCCGCCATTCCACATTCAGT3' (SEQ ID 140:2), --

UNITED STATES PATENT AND TRADEMARK OFFICE
CERTIFICATE OF CORRECTION

PATENT NO. : 6,869,760 B2
APPLICATION NO. : 09/263981
DATED : March 22, 2005
INVENTOR(S) : Paul B. Fisher It is certified that error appears in the above-identified patent and that said Letters Patent is hereby corrected as shown below:

In the Claims (cont'd):
Col. 20, One 4: "5' ATGGGGGTAGAGCACTGAATG3' , (SEQ ID NO:3)" should read
-- 5' ATGGGGGTAGAGCACTGAATG3' (SEQ ID NO:3), --
Col. 20, line 5: "5' AACACCAGCAGCAACAATCAG3' , (SEQ ID NO:4)" should read
-- 5' AACACCAGCAGCAACAATCAG3' (SEQ ID NO:4), and --
Col. 20, line 6: "5' AAATTAAGCTATGCAGTCGG3' . (SEQ ID NO:5)." should read
-- 5' AAATTAAGCTATGCAGTCGG3' (SEQ ID NO:5). --

Signed and Sealed this

Thirty-first Day of July, 2007

JON W. DUDAS
*Director of the United States Patent and Trademark Office*